(12) United States Patent
Gotani

(10) Patent No.: US 7,572,253 B2
(45) Date of Patent: Aug. 11, 2009

(54) SURGICAL OPERATION DEVICE

(75) Inventor: Hiroyuki Gotani, Osaka (JP)

(73) Assignee: Japan Science and Technology Agency, Saitma (JP)

( * ) Notice: Subject to any disclaimer, the term of this patent is extended or adjusted under 35 U.S.C. 154(b) by 199 days.

(21) Appl. No.: 10/551,641

(22) PCT Filed: Mar. 24, 2004

(86) PCT No.: PCT/JP2004/004098

§ 371 (c)(1),
(2), (4) Date: Aug. 14, 2006

(87) PCT Pub. No.: WO2004/086996

PCT Pub. Date: Oct. 14, 2004

(65) Prior Publication Data

US 2006/0282063 A1  Dec. 14, 2006

(30) Foreign Application Priority Data

Mar. 31, 2003 (JP) .............................. 2003-095905

(51) Int. Cl.
| | | |
|---|---|---|
| *G05B 19/18* | (2006.01) | |
| *A61B 17/00* | (2006.01) | |
| *A61B 17/42* | (2006.01) | |
| *A61B 17/06* | (2006.01) | |
| *A61B 19/00* | (2006.01) | |
| *A61B 1/00* | (2006.01) | |
| *A61D 1/06* | (2006.01) | |
| *G06F 19/00* | (2006.01) | |
| *B25J 17/00* | (2006.01) | |

(52) U.S. Cl. ............... 606/1; 74/490.01; 74/490.06; 128/897; 600/146; 600/102; 606/125; 606/137; 606/222; 700/3; 700/66; 700/245

(58) Field of Classification Search ............... 700/3, 700/66, 245; 600/1, 137, 146; 74/490.01, 74/490.06; 606/222; 128/897
See application file for complete search history.

(56) References Cited

U.S. PATENT DOCUMENTS 4,941,466 A * 7/1990 Romano ................ 606/80

(Continued)

FOREIGN PATENT DOCUMENTS

JP        6-210581 A        8/1994

(Continued)

OTHER PUBLICATIONS

Hiroyuki Gotani, M.D. et al., "Robotic manipulator system for microsurgery (first report)," *CARS 2000*, p. 1801.

(Continued)

*Primary Examiner*—Albert DeCady
*Assistant Examiner*—Thomas H Stevens
(74) *Attorney, Agent, or Firm*—Harnes, Dickey & Pierce PLC

(57) ABSTRACT

In order to rotate and move an arm of a slave which supports a needle-holder, the rotation and movement of a pen-shaped operating section (31) caused by the fingers of the operator's hand are directly transmitted as the rotation and movement of the needle-holder, as sensors for detecting the rotation and movement of the operating section, an X-axis torque sensor, Y-axis torque sensor, Z-axis torque sensor, and a rotation detecting potentiometer (33) are installed thereon. As a result, the rotation and movement of the pen-shaped operating section (31) caused by the fingers of the operator's hand are transmitted as the rotation and movement of the needle-holder in optimum proportions through a computing section. Therefore, when the needle-holder is to be finely moved, a subtle motion of the fingers of the hand can be satisfactorily transmitted. Thereby, it is possible to provide a surgical operation device capable of doing minute surgical operations with ease.

18 Claims, 3 Drawing Sheets

U.S. PATENT DOCUMENTS

| | | |
|---|---|---|
| 5,876,325 A | 3/1999 | Mizuno et al. |
| 6,120,433 A | 9/2000 | Mizuno et al. |
| 6,731,988 B1 * | 5/2004 | Green ........................... 700/3 |

FOREIGN PATENT DOCUMENTS

| | | |
|---|---|---|
| JP | 7-136173 A | 5/1995 |
| JP | 7-184929 A | 7/1995 |
| JP | 7-194609 A | 8/1995 |
| JP | 07-266263 | 10/1995 |
| JP | 8-117238 A | 5/1996 |
| JP | 8-299363 A | 11/1996 |
| JP | 2001-137257 A | 5/2001 |
| JP | 2002-059380 A | 2/2002 |
| JP | 2003-316493 | 11/2003 |

OTHER PUBLICATIONS

Bjorn D. Krapohl, M.D. et al., "Computer-Guided Microsurgery: Surgical Evaluation of a Telerobotic Arm," Wiley-Liss, Inc. 2001, pp. 22-29.

Hiroyuki Gotani, M.D. et al., "Robotic Manipulator System for Microsurgery," *The 12th Conference of Computer Aided Diagnosis of Medical Image, 11th Conference of Japan Society of Computer Aided Surgery, 2002*, pp. 85-86.

Hiroyuki Gotani, M.D. et al., "Robotic Manipulator System for Microsurgery (second report)," *The 29th Annual Meeting of Japanese Society of Reconstructive Microsurgery*, 2002, p. 154.

* cited by examiner

SURGICAL OPERATION DEVICE

TECHNICAL FIELD

The present invention relates to a surgical operation device using a master and a slave for performing a micro surgical operation.

BACKGROUND ART

Various surgical operation devices using a master and a slave for performing an operation have been developed; examples thereof can be found in the following references:
Japanese Unexamined Patent Publication No. 2001-137257 (published on May 22, 2001),
Japanese Unexamined Patent Publication No. 7-136173 (published on May 30, 1995),
Japanese Unexamined Patent Publication No. 7-194609 (published on Aug. 1, 1995),
Japanese Unexamined Patent Publication No. 8-117238 (published on May 14, 1996),
Japanese Unexamined Patent Publication No. 7-184929 (published on Jul. 25, 1995),
Computer-guided Microsurgery: Surgical Evaluation of a Telerobotic Arm (Microsurgery Vol. 21, No. 1 (2001), pp. 22-29).

Japanese Unexamined Patent Publication No. 2001-137257 discloses a remote manipulation device, as a master, having multiple pivots, and, for observing/treating an intravital site, a medical-use manipulator, which acts as a slave that is activated by remote manipulation of the remote manipulation device and includes multiple pivots. It also discloses controlling movement of the medical-use manipulator in accordance with manipulation information transmitted from the remote manipulation device.

Among the reference art disclosed in the above references, that with the object of performing laparoscopic, abdominal surgery by using a robot is not intended to suture appendicular microvessels. The reference "Computer-guided Microsurgery: Surgical Evaluation of a Telerobotic Arm" (Microsurgery Vol. 21, No. 1 (2001), pp. 22-29) has as an object of performing microsurgery, but a joystick-type operation appliance is employed therein.

When microsurgery such as rejoining a severed finger is performed, a bayonet-type appliance, such as a needle-holder, a pair of scissors, or pair of tweezers, is used for carrying out exfoliation, suturing or the like of a microvessel, nerve or the like. The microsurgery may be performed with these appliances. When a peripheral joint below the elbow is used to move an appliance, then either a finger or a hand holding an appliance moves the appliance, or movement of a hand/wrist/carpal joint moves the appliance. Here, there is considered to be 8 degrees of freedom in the movement of the appliance. However, there is no master arm or operation device that intuitively propagates the movement of a hand/wrist/carpal joint or a finger that operates the surgical appliance to a slave arm.

The present invention is made in view of the problem described above and has as an object to provide a surgical operation device on which an operator conducts real movement of a hand/wrist/carpal joint, a hand, or a finger as though operating a surgical appliance during surgery so that a multiple pivot slave arm is easily manipulated.

DISCLOSURE OF INVENTION

In order to achieve the above object, a surgical operation device in connection with the present invention is characterized in that the surgical operation device includes (1) a master that detects movement of a body of an operator and (2) a slave that performs surgery on tissue by moving in accordance with information on the detected movement of the body of the operator, the information being supplied from the master, the slave including a holder for holding a surgical appliance or an affected area. When an arbitrary orthogonal coordinate system in a space is labeld with XYZ coordinate axes, the master includes (1) a distal operation section that is to be held by a finger of the operator, (2) a first sensor that detects pressure applied on the distal operation section by the finger of the operator, (3) a second sensor that detects movement of the distal operation section in an orientation of X, (4) a third sensor that detects movement of the distal operation section in an orientation of Y, (5) a fourth sensor that detects movement of the distal operation section in an orientation of Z, (6) a fifth sensor that detects rotation of the distal operation section about a Z-axis, (7) a sixth sensor that detects flexion/extension of a wrist of the operator, (8) a seventh sensor that detects ulnar/radial deviation of the wrist of the operator, and (9) an eighth sensor that detects rotation of the wrist of the operator. When an orientation of forward/backward movement of the holder is labeled as a Z'-axis, and axes each of which are orthogonal to the Z'-axis are labeled as an X'-axis and a Y'-axis, the X'Y'Z' coordinate axes being an orthogonal coordinate system, the slave includes an arm supporting the holder. Further, the holder includes (1) a nipping section pinching an operation appliance or an affected area and (2) a base section supporting the nipping section. Further, the nipping section increases/reduces degree of nipping in reaction to pressure applied to the distal operation section and detected by the first sensor. Further, the base section moves in the respective orientations of X', Y', and/or Z' corresponding to respective movement amounts detected by the second sensor to the fourth sensor, and rotates about the Z' axis corresponding to rotation amount detected by the fifth sensor. Further, the arm rotates on respective joints provided in the arm corresponding to amount and orientation of movement detected by the sixth sensor and the seventh sensor, and rotates on an inner axis in accordance with a rotation amount detected by the eighth sensor.

In the above structure, with the first sensor to the eighth sensor, not only wrist rotation of the operator but also subtle biasing (movement or rotation) of the distal operation section by the finger of the operator can be transmitted to the slave.

Therefore, when it is desired to make the holder move subtly, the operator can make the holder of the slave move as the finger of the operator moves, without combining various rotations and movements of the arm of the slave.

This enables microsurgery to be easily performed by using the surgical operation device.

The master may include a distal operation section that rotates as the operator rotates it with his/her finger. The slave may have an arm that is to be in direct contact with an affected area, and may include a holder that rotates about an axis defined by a line that passes through a point connecting the arm and the affected area, and a point inside of the arm, corresponding to a rotation transmitted from the distal operation section.

Further, in addition to the structure described above, a surgical operation device in connection with the present invention is characterized in that the second sensor to the fourth sensor are a torque sensors.

In the above structure, because the second sensor to the fourth sensor are torque sensors, it is possible to input operator-intended-movement by applying subtle forces. In addition, because the movement ratio is changeable through the calculation section, the movement can be transmitted as enlarged movement. Moreover, a weight of a glove can be reduced, as an additional effect. Therefore, the operator would not be required to make large movements of his/her hand in order to move the holder. In other words, small movements of the hand of the operator are sufficient to transmit the movement. Accordingly, in addition to the effect in the above structure, because the movement ratio can be changed by calculation, the surgery can be more easily performed by using the surgical operation device. As described above, the movement ratio between the master and the slave is variable, and the movement ratio may vary in different axes.

For a fuller understanding of the nature and advantages of the invention, reference should be made to the ensuing detailed description taken in conjunction with the accompanying drawings.

BEST MODE FOR CARRYING OUT THE INVENTION

Figure 1:
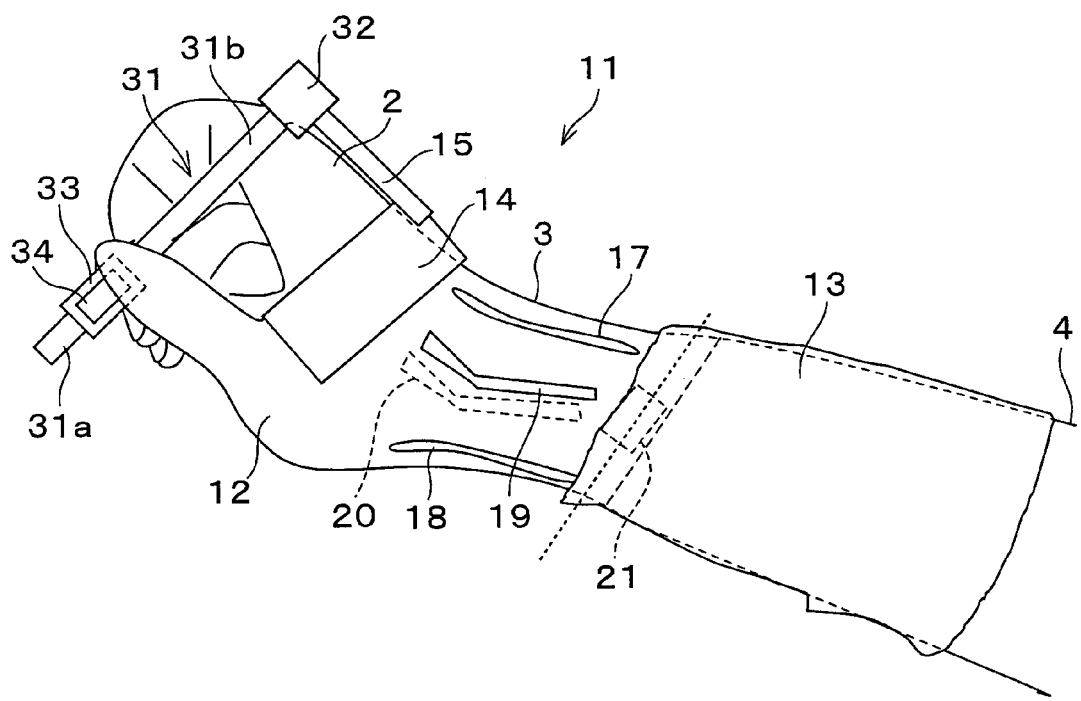
FIG. 1(a) is a perspective view that illustrates a structure of a master in a surgical operation device in connection with the present invention.
FIG. 1(b) is a cross section that illustrates a wrist and a forearm-cover.
Figure 1:
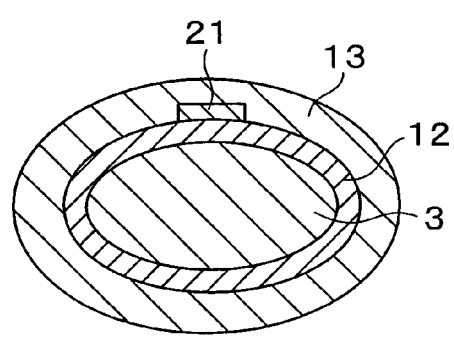

The following describes an embodiment of the present invention.

A surgical operation device in connection with the embodiment performs surgical operations, mainly separation or suture of micro tissue such as a vessel, a nerve, or lymph duct, and includes a micro-soft-tissue-suture-assisting manipulator as a slave.

In order to suture a microvessel (especially one having a diameter of 1 mm or less), it is necessary to grip a needle-holder with a right hand unit and to precisely insert a needle point of a 10-0 or 11-0 suture needle (10-0 and 11-0 are part numbers of the suture needle), in which the tip of the suture needle is approximately between 5 μm and 70 μm, into the vessel wall at a right angle. In order to do so, it is necessary to use an appliance acting as a needle-holder, the end of which is capable of sensitive movement.

Generally, in a micro suture operation, the right hand rotates a hand joint to adjust the tip of the needle in such a way that the tip of the needle becomes orthogonal to the vessel wall. At the time when the tip of the needle approaches the vessel wall, an appliance held with a thumb, forefinger, and middle finger is subtly rotated along a curvature of the needle. Moreover, the vessel may move slightly while the edge of the needle is passing through the vessel wall. Therefore, at this time, the operator needs to adjust the rotation axis of the appliance in the X-orientation, in the Y-orientation, or in the Z-orientation.

A lumen of a microvessel is often closed. When that is the case, it is necessary to widen the lumen of the microvessel by using a pair of micro tweezers held with a left hand unit. In order to widen the lumen of the microvessel, the pair of tweezers on the left-hand side need to be inserted approximately between several-hundred-μm and one-mili-meter into the lumen of the vessel on the right-hand side in such a way that the pair of tweezers are made to be parallel to a stream of the vessel and at an angle of around 30 degrees with respect to the horizontal plane. In addition, an opening angle of the pair of tweezers needs to be precisely controlled so that the ends of the tweezers open with a width between several-hundred-μm and 1 mm, corresponding to the diameter of the vessel that is to be broadened. In this situation, orientations of the appliances on both the right side and the left side need to be orthogonal to each other.

Subsequently, the needle is passed through the vessel wall down to the base of the needle and is pulled out from the lumen of the vessel using the pair of tweezers on the left side and the needle-holder on the right side. The pulled-out micro needle is again held by the needle-holder on the right side, and is passed from the lumen to the vessel wall on the opposite side. The thread is pulled with both the right side unit and the left side unit.

The thread is held by the right side unit and is pulled out from the vessel wall on the opposite side, the thread is then looped on the pair of tweezers on the left side. A stump of the thread hanging out from the first vessel wall is held by the left side unit. Being pulled from both sides, the thread is tied. Here, the operation region of the ends of the respective appliances on the right-hand side and the left-hand side need to overlap without the ends of the appliances coming into contact with each other.

Figure 2:
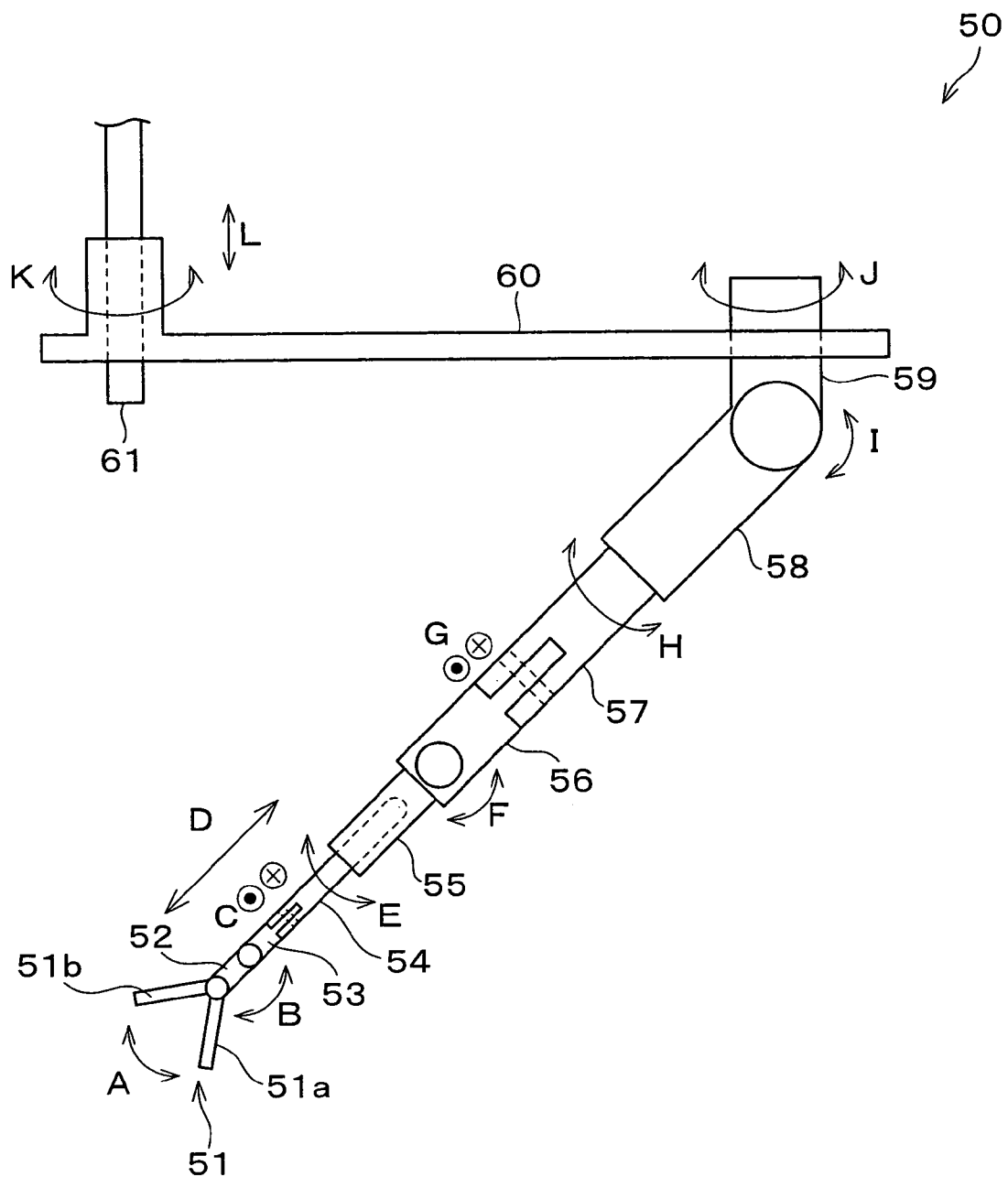
FIG. 2 is a plane view that illustrates a structure of the slave.

A manipulator that can actualize the foregoing operation is constructed as described in FIG. 2. An operation region for rejoining of a severed finger is considered to be approximately 10 cm×10 cm×5 cm (size of a hand).

A manipulator 50 includes an arm for adjusting the manipulator 50 so that the targeted vessel is placed within an operation region of the manipulator 50, and a bar 60 and a first pivot 61, both of which are for coarse positioning of the arm. The term "arm" is a generic term for a fifth processing section 55, a sixth processing section 56, a seventh processing section 57, an eighth processing section 58, and a second pivot 59.

On the end of the arm, a needle used for actual suturing of a vessel and a holder that holds an affected area are installed. The holder is constructed of a nipping section and a base section. The nipping section is formed of a first processing section 51. The base section is a generic term for a second processing section 52, a third processing section 53, and a fourth processing section 54. The first processing section 51 includes a first nipping piece 51a and a second nipping piece 51b. Opening and closing the first nipping piece 51a and the second nipping piece 51b enables these nipping pieces to work as a needle-holder that holds a needle. The first processing section 51 may work as a pair of tweezers, as well as a needle-holder, to pinch the affected area.

The first nipping piece 51a and the second nipping piece 51b of the first processing section 51 may open and close in the orientation of A, as indicated in the figure. The second processing section 52 rotates upward and downward in the orientation of B, as indicated in the figure. The third processing section 53 horizontally rotates in the orientation of C, as indicated in the figure. The fourth processing section 54 axially extends and retracts along the orientation of D, as indicated in the figure. The fifth processing section 55 causes rotation about the axis, in the orientation of E, as indicated in the figure. The sixth processing section 56 causes upward and downward rotation in the orientation of F, as indicated in the figure. The seventh processing section 57 causes horizontal rotation in the orientation of G, as indicated in the figure. The eighth processing section 58 causes rotation about the axis in the orientation of H, as indicated in the figure. The second pivot 59 causes upward and downward rotation in the orientation of I as indicated in the figure. The bar 60 rotates on the axis in the orientation J as indicated in the figure. The first pivot 61 allows rotation about the axis in the orientation of K, as indicated in the figure. The first pivot 61 also axially extends and retracts along the orientation of L, as indicated in the figure.

In order to actualize the hand movement described above with the manipulator 50, the manipulator 50 rotates at least 25 degrees in the radial deviation and 55 degrees in the ulnar deviation about a point inside in the section corresponding to the wrist of the operator, the rotation corresponding to the ulnar deviation and the radial deviation of the operator. Further, the manipulator 50 vertically rotates at least minus 30 degrees to plus 70 degrees about the inner point, corresponding to the flexion and the extension of the wrist of the operator. Further, the manipulator 50 rotates 180 degrees about the axis connecting two inner points, corresponding to the rotation of the wrist of the operator. Further, when two arbitrary orthogonal coordinates in a space define X'Y'Z' coordinate axes, the manipulator rotates at least ±30 degrees horizontally about an inner point of the section corresponding to the finger of the operator, the rotation corresponding to the movement of the finger of the operator in the X'-orientation. Further, the manipulator vertically rotates at least minus 45 degrees to plus 70 degrees about an inner point, corresponding to the movement of the finger of the operator in the Y'-orientation. Further, the manipulator rotates 180 degrees on the axis connecting two inner points, corresponding to the rotation of the wrist of the operator. Further, the manipulator extends at least 5 cm parallel to an axis connecting two inner points, corresponding to the movement of the finger of the operator in the Z'-orientation. The manipulator may be movable in a wider region including the region mentioned above.

On the other hand, the surgical operation device includes a master 11 as illustrated in FIG. 1(*a*) that can give all necessary commands to the manipulator 50. A right hand is used as an example here, but the right hand may be replaced with a left hand. Two manipulators are prepared so as to be respectively controlled by left and right hands. The right hand side is made to be the needle-holder, and the left hand side is made to be the pair of tweezers. It is usual to prepare masters and slaves sufficient for both hands. In a case in which there is one surgeon and one assistant, four masters and four slaves may be concurrently used.

The numbers "2", "3", and "4" respectively indicate a hand, a wrist, and a forearm of the operator.

"12" is an operator-worn glove (hand glove) including a sensor. The operator-worn glove is made to cover the wrist 3 of the operator. Fingers are exposed. A metal plate 14 and a metal bar 15 are installed on the operator-worn glove 12, and two three-axis torque sensors 32 are tightly fixed on the operator-worn glove 12 via the metal bar 15.

A pen-shaped operation section 31 is stick-shaped, and an operator can grip it in the same way as a pencil is held with the fingers. The pen-shaped operation section 31 includes a pen-shaped operation section front part 31*a*, which is the tip of the pen-shaped operation section, and a pen-shaped operation section rear part 31*b*, which is behind the pen-shaped operation section front part 31*a*. On the pen-shaped operation section rear part 31*b*, the torque sensor 32 is fixed. The pen-shaped operation section front part 31*a* can be rotated about the line that connects two points in the pen-shaped operation section 31, with a torque the operator applies using his/her finger. The rotation detection potentiometer 33 (fifth sensor) that measures the rotation of the pen-shaped operation section front part 31*a* is fixed on the pen-shaped operation section rear part 31*b*.

A pressure-sensitive sensor 34 (first sensor) made of a pressure-sensitive sensor material is adhered to a surface of the rotation detection potentiometer 33. This makes it possible to measure pressure applied to the pressure-sensitive sensor 34 by the finger of the operator. The holder of the manipulator 50, that is the first processing section 51, can be opened and closed, depending upon the intensity of the pressure.

In a condition in which two arbitrary orthogonal coordinates in a space define XYZ coordinate axes, the torque sensor 32 functions as an X-axis orientation torque sensor (second sensor), a Y-axis orientation torque sensor (third sensor), and an Z-axis orientation torque sensor (fourth sensor). This structure can be realized with, for example, a three-axis torque sensor. Instead of using a material having the functions of these three sensors by itself, three individual sensors may be prepared. This makes it possible to determine a torque on the pen-shaped operation section 31 about the X-axis, the Y-axis, and the Z-axis. The Z-axis is oriented along a direction in which the pen-shaped operation section 31 moves forward and backward along its axis (long axis). The X-axis and the Y-axis are axes that are respectively orthogonal to the Z-axis. In other words, when the pen-shaped operation section 31 is rotated toward one orientation of the rotation detection potentiometer 33 it is rotated about the X-axis. When the pen-shaped operation section 31 is rotated toward another orientation of the rotation detection potentiometer 33 it is rotated about the Y-axis. The Y-axis is orthogonal to the X-axis. The torque in the respective orientations of X, Y, and Z applied by the hand of the operator is converted into a movement amount by calculations conducted by the calculation section 82 (see FIG. 3). The conversion ratio here is variable. In addition, the rotation detection potentiometer 33 supplies the rotation amount. Since the pen-shaped operation section 31 can actually be rotated, it is possible to detect four degrees of freedom (movement parallel to the respective X, Y, and Z axes, and rotation detected by the rotation detection potentiometer 33) at the end of the arm.

The respective amounts of change detected by the respective sensors (first sensor to eighth sensor) of the master, including the torque sensors and the others, are supplied to the calculation section 82 and are converted into a movement amount of the actuator. The conversion ratio used for the conversion may be arbitrarily changed by the user (surgeon or the like). The movement ratio may vary in different axes.

The operator-worn glove 12 covers the wrist 3 of the surgeon and exposes the finger part from the wrist 3 to the hand 2 so as to allow the surgeon to grip the pen-shaped operation section 31 with his/her finger.

Four sensors are adhered to the wrist section of the operator-worn glove 12. "17" is an ulnar deviation sensor (seventh sensor) that detects rightward twisting of the wrist by using a twisting sensor. "18" is a radial deviation sensor (seventh sensor) that detects leftward twisting of the wrist by using a twisting sensor. "19" is an extension sensor (sixth sensor) that detects extension of the wrist by using a twisting sensor. On the rear side of the wrist 3, a flexion sensor 20 (sixth sensor) that detects flexion of the wrist by using a twisting sensor is adhered at the position opposite to the extension sensor 19. As the foregoing describes, the twisting sensors make it possible to detect the movement of the wrist in two orientations (ulnar/radial deviation orientation, flexion/extension orientation).

A photo sensor 21 (eighth sensor) is adhered at the rear of the wrist, to the wrist-end section of the operator-worn glove 12. The photo sensor 21 is a photo sensor for detecting inward/outward rotation of the forearm and rotation of the wrist. The forearm-cover 13 is disposed at the position overlapping the wrist-end section of the operator-worn glove 12 so that the photo sensor 21 is covered. FIG. 1(b) illustrates the cross section along the dotted line portion.

When the wrist is rotated, the photo sensor 21 measures the rotation amount of the operator-worn glove 12 with respect to the forearm-cover 13. This can be achieved by placing a random pattern on the inner side of the forearm-cover 13. Accordingly, the photo sensor 21 makes it possible to detect the rotation of the wrist 3.

If such a surgical operation device is employed, the nipping section increases/decreases the degree of pinching in reaction to the pressure applied to the pen-shaped operation section 31 and detected by the pressure-sensitive sensor 34 placed thereon. The base section respectively moves along the X'-axis orientation, the Y'-axis orientation, and the Z'-axis orientation, corresponding to the movement amount detected by the respective torque sensors in the X-axis orientation, in the Y-axis orientation, and in the Z-axis orientation. The base section also rotates corresponding to the rotation amount detected by the rotation detection potentiometer 33. Further, the arm rotates on the respective joints in the arm, corresponding to the amount and orientation of movement detected by the ulnar deviation sensor, the radial deviation sensor, the extension sensor, and the flexion sensor 20. The arm also rotates on the inner axis, corresponding to the rotation amount detected by the photo sensor 21.

Figure 3:
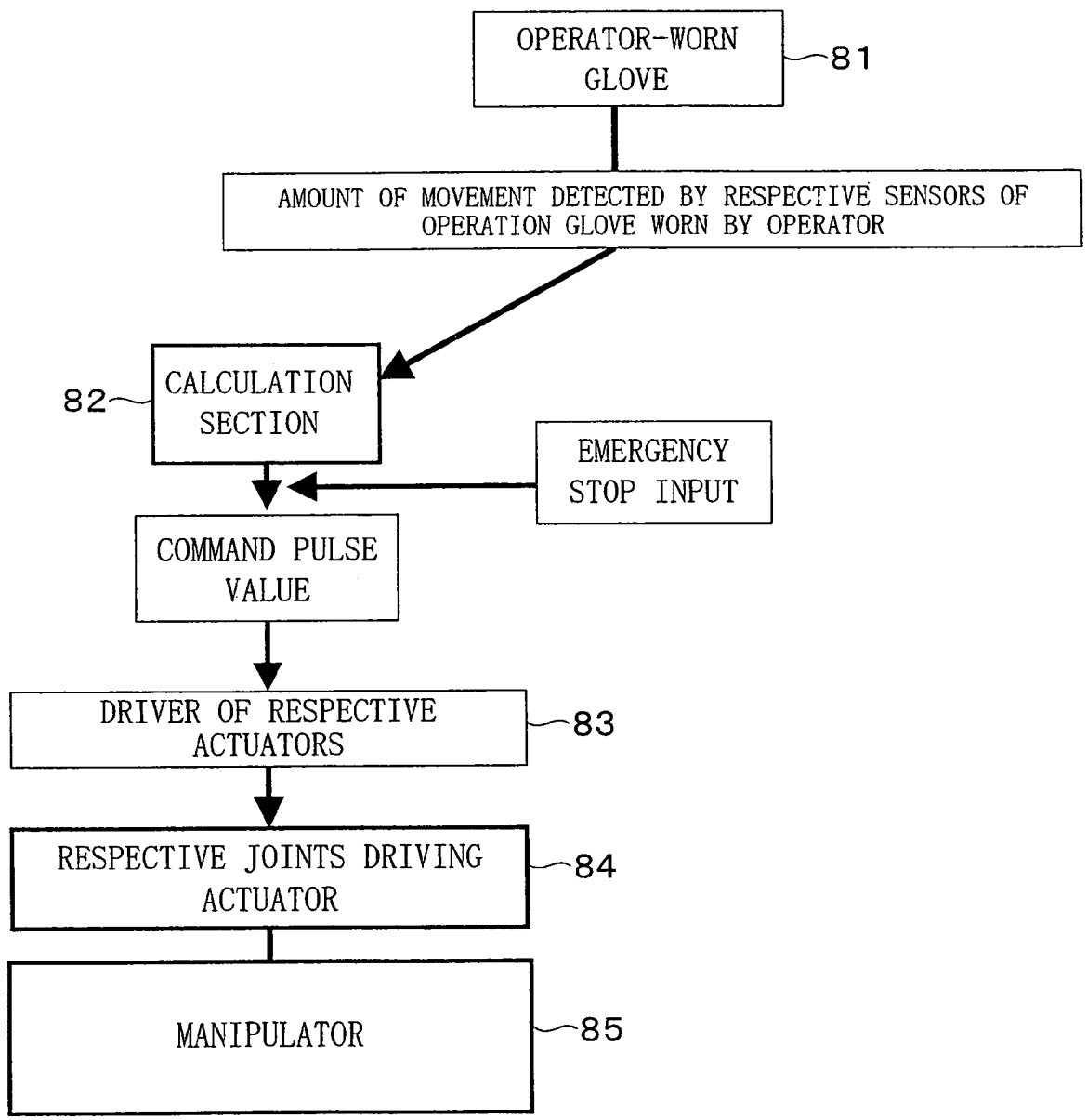
FIG. 3 is a block diagram that illustrates a structure of the surgical operation device in connection with the present invention.

As illustrated in FIG. 3, on the master, an operator-worn glove 81 (same as 12) is provided. On the slave, a driver 83 of respective actuators, a respective-joint-driving actuator 84, and a main body of a manipulator 85 are disposed. On the master or on the slave, a calculation section 82 is disposed. Movement amounts detected by the respective sensors of the operator-worn glove are inputted from the operator-worn glove 81 to the calculation section 82. As described above, the torque measured by the torque sensors is converted here into a movement amount by designated movement ratios. The movement ratios between the respective axes are variable. The calculation section 82 transmits the information on the movement amount as a command pulse value to the driver 83 of the respective actuators. A signal for emergency stop of the manipulator is transmitted also as a command pulse value. The driver 83 of the respective actuators converts the supplied command pulse value into a command signal for the respective-joint-driving actuators 84. The respective-joint-driving actuators 84 operate the manipulator main body 85 in accordance with the command signal.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

The present invention may be applicable to a device such as a surgical operation device for performing a micro surgical operation by using a master and a slave.

The invention claimed is:
1. A surgical operation device comprising a master that detects movement of a body of an operator and a slave that performs surgery on tissue by moving in accordance with information on the detected movement of the body of the operator, the information supplied from the master, the slave comprising a holder for holding an operation appliance or an affected area, wherein:

when an orthogonal coordinate system in a space is formed of XYZ coordinate axes, the master comprises:
an distal operation section that is to be held by a finger of the operator;
a first sensor that detects a pressure applied on the distal operation section by the finger of the operator;
a second sensor that detects movement of the distal operation section along an orientation of an X-axis;
a third sensor that detects movement of the distal operation section along an orientation of a Y-axis;
a fourth sensor that detects movement of the distal operation section in along an orientation of a Z-axis;
a fifth sensor that detects rotation of the distal operation section about the Z-axis;
a sixth sensor that detects flexion/extension of a wrist of the operator;
a seventh sensor that detects ulnar/radial deviation of the wrist of the operator; and
an eighth sensor that detects rotation of the wrist of the operator; and
when an orientation of forward/backward movement of the holder is indicated by Z'-axis, and axes each of which are orthogonal to the Z'-axis are indicated by an X'-axis and a Y'-axis, the X'Y'Z' coordinate axes being an orthogonal coordinate system,
the slave comprises an arm supporting the holder;
the holder comprises a nipping section for pinching an operation appliance or an affected area, and a base section supporting the nipping section;
the nipping section increases/reduces a degree of pinching in reaction to the pressure applied to the distal operation section and detected by the first sensor;
the base section moves respectively along orientations of the X', Y', and/or Z' axes corresponding to respective movement amounts detected by the second sensor to the fourth sensor, and rotates about the Z'-axis corresponding to a rotation amount detected by the fifth sensor; and
the arm rotates on respective joints in the arm corresponding to amount and orientation of movement detected by the sixth sensor and by the seventh sensor, and rotates on an inner axis in accordance with a rotation amount detected by the eighth sensor.

2. A surgical operation device as set forth in claim 1 wherein the second sensor to the fourth sensor are torque sensors.

3. A surgical operation device as set forth in claim 2, further comprising a calculation section that converts torque measured by the torque sensors into movement amounts of respective sections of the slave, by using designated movement ratios.

4. A surgical operation device as set forth in claim 3 wherein the movement ratios in the calculation section are variable.

5. A surgical operation device as set forth in claim 4 wherein the movement ratios vary in different sections of the slave.

6. A surgical operation device as set forth in claim 1 wherein the distal operation section is pen-shaped.

7. A surgical operation device as set forth in claim 1 wherein the first sensor to the eighth sensor are disposed on an operator-worn glove shaped in such a way as to cover the wrist of the operator and expose the finger of the operator.

8. A surgical operation device as set forth in claim 1 wherein the eighth sensor is disposed on an operator-worn glove that is shaped in such a way as to cover the wrist of the operator and expose the finger of the operator, and the eighth sensor measures rotation amount of the operator-worn glove with respect to a forearm-cover covering a forearm of the operator.

9. A surgical operation device as set forth in claim 1 wherein the nipping section opens and closes so as to pinch the operation appliance.

10. A surgical operation device as set forth in claim 9 wherein the operation appliance is a suture needle.

11. A surgical operation device as set forth in claim 1 wherein the nipping section opens and closes so as to pinch the affected area.

12. A surgical operation device as set forth in claim 1 wherein the base section rotates and moves at least ±30 degrees horizontally on an inner joint, corresponding to the movement amount detected by the second sensor.

13. A surgical operation device as set forth in claim 1 wherein the base section rotates and moves at least minus 45 degrees to plus 70 degrees vertically on an inner joint, corresponding to the movement amount detected by the third sensor.

14. A surgical operation device as set forth in claim 1 wherein the base section extends at least 5 cm parallel to an axis connecting two inner points, corresponding to the movement amount detected by the fourth sensor.

15. A surgical operation device as set forth in claim 1 wherein the base section rotates 180 degrees on an axis connecting two inner points, corresponding to the rotation amount detected by the fifth sensor.

16. A surgical operation device as set forth in claim 1 wherein the arm rotates at least minus 30 degrees to plus 70 degrees vertically on an inner joint, corresponding to the amount and orientation of the movement detected by the sixth sensor.

17. A surgical operation device as set forth in claim 1 wherein the arm rotates at least 25 degrees in radial deviation and 55 degrees in ulnar deviation on an inner joint, corresponding to the movement amount and movement orientation both of which have been detected by the seventh sensor.

18. A surgical operation device as set forth in claim 1 wherein the arm rotates 180 degrees on an axis connecting two inner joints, corresponding to the rotation amount detected by the eighth sensor.

* * * * *